(12) United States Patent
Tu et al.

(10) Patent No.: US 6,506,398 B1
(45) Date of Patent: Jan. 14, 2003

(54) DEVICE FOR TREATING DIABETES AND METHODS THEREOF

(76) Inventors: Hosheng Tu, 2151 Palermo, Tustin, CA (US) 92782; Rodolfo C. Quijano, 27451 Lost Trail La., Laguna Hills, CA (US) 92653

( * ) Notice: Subject to any disclaimer, the term of this patent is extended or adjusted under 35 U.S.C. 154(b) by 0 days.

(21) Appl. No.: 09/583,296

(22) Filed: May 31, 2000

Related U.S. Application Data

(63) Continuation-in-part of application No. 09/560,208, filed on Apr. 28, 2000.

(51) Int. Cl.⁷ ............... A61F 2/00; A61F 2/06; A61K 38/00
(52) U.S. Cl. ............ 424/423; 514/2; 623/1.49
(58) Field of Search ............ 424/423; 514/2; 623/1.49

(56) References Cited

U.S. PATENT DOCUMENTS

| | | | |
|---|---|---|---|
| 4,806,595 A | * | 2/1989 | Noishiki et al. |
| 5,080,670 A | * | 1/1992 | Imamura et al. |
| 5,599,558 A | * | 2/1997 | Gordinier et al. |
| 5,785,965 A | * | 7/1998 | Pratt et al. |
| 5,871,769 A | | 2/1999 | Fleming et al. |
| 5,986,168 A | * | 11/1999 | Noishiki et al. |
| 6,040,157 A | * | 3/2000 | Hu et al. |

FOREIGN PATENT DOCUMENTS

JP  62026230 A  *  2/1987

OTHER PUBLICATIONS

Burgess A and Nicola N, *Growth Factors and Stem Cells*, Chapter 1, published by Academic Press 1983.

* cited by examiner

*Primary Examiner*—Jon P. Weber

(57) ABSTRACT

A vascular graft comprising Vascular Endothelial Growth Factor (VEGF) and/or Platelet Derived Growth Factor (PDGF) for enhanced site-specific angiogenesis and methods thereof are disclosed. At least one VEGF, PDGF or angiogenesis factor is incorporated into the vascular graft to facilitate enhanced angiogenesis so as the cells are stimulated to migrate to environments having higher concentration of growth factors and start mitosis.

6 Claims, 6 Drawing Sheets

DEVICE FOR TREATING DIABETES AND METHODS THEREOF

RELATIONSHIP TO COPENDING APPLICATION

This patent application is a continuation-in-part application of application Ser. No. 09/560,208 filed Apr. 28, 2000, the entire contents of which are incorporated herein by reference.

FIELD OF THE INVENTION

The present invention relates generally to improved medical device and methods for using same. More particularly, the present invention relates to a vascular graft implant comprising vascular endothelial growth factor (VEGF) and/or platelet derived growth factor (PDGF) for enhanced site-specific angiogenesis and methods thereof.

BACKGROUND OF THE INVENTION

The basic function of an arterial blood vessel is for transportation of blood from the heart to organs and tissues of the body. When a blood vessel is diseased or becomes dysfunctional, a vascular graft is usually employed for implantation to replace or assist the diseased or dysfunctional blood vessel. The vascular grafts include autologous blood vessel, homograft, cryo-preserved blood vessel, grafts made of synthetic material such as expanded polytetrafluoroethylene (e-PTFE) or polyester (trade name Dacron), and grafts made of biological material, such as bovine internal mammal artery, human umbilical vein, or pericardium.

A special sub-group that has dysfunctional blood vessels belongs to diabetic patients. Diabetes mellitus is characterized by a broad array of physiologic and anatomic abnormalities, for example, altered glucose disposition, hypertension, retinopathy, abnormal platelet activity, aberrations involving medium and small sized vessels, and other problems. Diabetics may depend on insulin for the prevention of ketoacidosis. Developed atrophic ulcer and infected alterations of the foot as a result of complications of diabetes mellitus may require foot amputation. The current treatment may include drug therapy, for example, U.S. Pat. No. 5,871,769 to Fleming et al. discloses methods for the prevention and/or treatment of diabetes mellitus using magnesium gluconate. However, a biocompatible vascular graft may be implanted to enhance blood circulation and eventually extremity salvage. A vascular graft having enhanced angiogenesis capability or having angiogenesis factors may promote peripheral revascularization or neovascularization for blood perfusion so as to save the diseased foot from amputation. The process of angiogenesis (new capillary formation) is stimulated by angiogenesis factors.

The vascular graft or prosthesis made of synthetic materials is usually porous, compliant, strong, and biocompatible. The micropores of a synthetic prosthesis are believed to facilitate tissue/cells ingrowth from the host so as to accelerate the healing process. It is also suggested that the host cells tend to encapsulate a foreign substrate if the host tissue does not achieve cell infiltration into the substrate. In clinical practices, partially clotted blood, collagen, gelatin or other gelatinous material may be coated upon/into the micropores so that blood leakage during the initial phase of implantation is minimized. U.S. Pat. No. 5,851,230 discloses a vascular graft with a collagen sealant, and the patent is incorporated herein by reference.

The vascular prosthesis made of biological material contains collagen as its major component. A biological prosthesis is usually crosslinked to reduce the antigenicity, enhance its antithrombogenicity, and/or improve the durability. Typical crosslinking agents include glutaraldehyde, formalin, dialdehyde starch, polyepoxy compounds or the like. U.S. Pat. No. 4,082,507 discloses a treatment method with glutaraldehyde, dialdehyde starch and formalin. U.S. Pat. No. 4,806,595 discloses a treatment method with polyepoxy compounds and/or heparin. The implantation with a polyepoxy compounds treated graft usually exhibit much tissue regeneration and capillary proliferation, and may account for some degree of angiogenesis. Both patents are incorporated herein by reference.

When a vascular graft is placed in a human body, the inner walls of the graft may become lined with endothelial cells, which possess antithrombotic properties for preventing blood clotting and deposition of blood thrombus on the inner walls. In actual clinical situations, however, lining by the endothelial cells is usually extremely delayed, and in most cases, only the area of the anastomosis of the vascular graft becomes covered with endothelial cells while remote locations away from the anastomoses are not covered. Accordingly, thrombus continues to deposit on the inner walls where endothelialization is void. Though endothelial seeding or sodding method has been recently developed to assist the endothelialization process, the seeded/sodded cells may separate from the inner wall of a vascular graft and be washed away by the blood stream. For example, U.S. Pat. No. 4,820,626 discloses a method of treating a synthetic or naturally occurring surface with microvascular endothelial cells. One of the major drawbacks is the extra step of collecting autologous endothelial cells, enzymatic digestion by collagenase, centrifugal filtration, and seeding prior to implantation of the graft.

Furthermore, U.S. Pat. No. 5,785,965 discloses a process for sodding modified cells onto a vascular prosthesis for implantation, wherein endothelial cells derived from subcutaneous adipose tissue are genetically modified to express the endothelial cell specific angiogenic factor VEGF. The method accelerates endothelialization on the luminal surface of the vessel. However, during the early stage of transplantation, the sodded cells may separate from the inner wall of a vascular graft and be washed away by the blood stream. It was reported that when endothelial seeding is applied to grafts installed in the canine infrarenal aorta, surface thromboresistance improves significantly over controls only after the seeded grafts have healed for approximately 4 weeks. In the above discussed endothelialization processes, only autologous endothelial cells may be used because of concerns on immunological response. In almost any cell transplantation procedure, immunological response is always a concern.

Noishiki et al. in U.S. Pat. No. 5,387,236 discloses a vascular prosthesis by depositing fragments of biological tissues such as vascular tissues, connective tissues, fat tissues and muscular tissues; and cells such as vascular endothelial cells, smooth muscle cells and fibroblast cells within the wall of a vascular prosthesis. Though the patent discloses a method for effectively depositing cells/tissues into the interstices of a vascular prosthesis, Noishiki et al. does not disclose a method of incorporating vascular endothelial growth factor or platelet derived growth factor to promote angiogenesis and to facilitate in situ proliferation of endothelial cells and/or neovascularization inside the walls of an implanted vascular prosthesis.

The angiogenesis process is believed to begin with the degradation of the basement members by proteases secreted from endothelial cells activated by mitogens such as vascular endothelial growth factor and basic fibroblast growth factor (bFGF). The cells migrate and proliferate, leading to the formation of solid endothelial cell sprouts into the stromal space, then, vascular loops are formed and capillary tubes develop with formation of tight junctions and deposition of new basement membrane. Recent studies have applied vascular endothelial growth factor to expedite and/or augment collateral artery development in animal models of myocardial and hindlimb ischemia. The relationship between growth factors, stem cells and cell progenitors has been documented (Burgess, A and Nicola N., *Growth Factors and Stem Cells*, Chapter 1, published by Academic Press 1983).

Vascular endothelial growth factor (VEGF) is mitogenic for vascular endothelial cells and consequently is useful in promoting neovascularization (angiogenesis) and reendothelialization. Angiogenesis means the growth of new capillary blood vessels. Angiogenesis is a multi-step process involving capillary endothelial cell proliferation, migration and tissue penetration. VEGF is a growth factor having a cell-specific mitogenic activity. It would be desirable to employ a wound healing substrate incorporating a mitogenic factor having mitogenic activity that is highly specific for vascular endothelial cells following vascular graft surgery, balloon angioplasty or to promote collateral circulation. U.S. Pat. No. 5,194,596 discloses a method for producing VEGF while U.S. Pat. No. 6,040,157 discloses a specific VEGF-2 polypeptide. Both patents are incorporated herein by reference.

U.S. Pat. No. 5,980,887 discloses a method to isolate EC progenitor from circulating blood and methods for enhancing angiogenesis with endothelial progenitor cells in a patient by administering to the patient an effective amount of an isolated endothelial progenitor cell, wherein the endothelial progenitor cell may include $CD34^+$, $flk-1^-$ or $tie-1^+$. However, Isner et al. in U.S. Pat. No. 5,980,887 does not disclose incorporating VEGF onto a medical prosthesis for localized site-specific angiogenesis enhancement.

Hammond et al. in U.S. Pat. No. 5,880,090 discloses methods for enhancing the endothelialization of synthetic vascular grafts by administering to a graft recipient an agent that mobilizes bone marrow derived $CD34^+$ cells into the blood stream, that enhances the adherence to graft surfaces of blood-borne endothelial progenitors. Again, immunological response to any cell transplantation is a clinical concern.

Gordinier et al. in U.S. Pat. No. 5,599,558 discloses a method of making a platelet releasate product and methods of treating tissues with the platelet releasate. Platelet derived growth factor (PDGF) is a well-characterized dimeric glycoprotein with mitogenic and chemoattractant activity for fibroblasts, smooth muscle cells and glial cells. In the presence of PDGF, fibroblasts move into the area of tissue needing repair and are stimulated to divide in the lesion space itself. It has been reported that the cells exposed to lower PDGF concentrations are stimulated to move to environments having higher concentrations of PDGF and divide. The patent is incorporated hereby by reference.

Uncontrolled over-angiogenesis or inappropriate angiogenesis is detrimental to a patient. This inappropriate angiogenesis is mostly related to non site-specific process and may result in proliferation of tumors and/or cancers. For example, it is only after many solid tumors are vascularized as a result of angiogenesis that the tumors begin to grow rapidly and metastasize. Because angiogenesis is so critical to these functions, it must be carefully regulated at any specific site or locality in order to maintain health.

A site-specific angiogenesis by incorporating VEGF and/or PDGF onto a medical material, particularly a cardiovascular device, may attract the progenitor cells, endothelial cells or the like from the circulating blood via a vascular graft to deposit onto the device surface and enhance the needed site-specific angiogenesis at the lesion site. Therefore, there is an urgent clinical need for a vascular graft having incorporated VEGF and/or PDGF onto the graft that may provide angiogenesis factors and circulating blood so as to enhance site-specific neovascularization and angiogenesis at the graft and its proximity to treat diabetic foot.

SUMMARY OF THE INVENTION

In general, it is an object of the present invention to provide a method for preparing a vascular graft having site-specific angiogenesis factor, preferably by incorporating vascular endothelial growth factor and/or platelet derived growth factor onto the vascular graft. The vascular graft of the present invention may be used to bypass or repair a part of the diseased/dysfunctional blood vessel. It is a further object of the present invention to provide a vascular graft having site-specific angiogenesis factors comprising incorporating at least one vascular endothelial growth factor, or at least one platelet derived growth factor, or other angiogenesis factor, and combination thereof onto the medical device.

In one preferred embodiment, the vascular graft having site-specific angiogenesis factor comprises at least one vascular endothelial growth factor. Vascular endothelial growth factor, which is also known as vascular permeability factor, is a secreted angiogenic mitogen whose target cell specificity appears to be restricted to vascular endothelial cells. The "angiogenesis factor" of the present invention refers to any compound, substrate, material, specie, factor, or element that stimulates or promotes angiogenesis activity. The angiogenesis factor may comprise one of the following: vascular endothelial growth factor, platelet derived growth factor, tissue treatment factor, and the like. The "vascular endothelial growth factor" in this invention refers broadly to any and all the members of the vascular endothelial growth factor family, which may comprise polynucleotides, polypeptides encoded by such polynucleotides that facilitate angiogenesis, and the like. U.S. Pat. No. 6,040,157 discloses general characteristics and specific properties of vascular endothelial growth factor and is incorporated herein by reference. VEGF has four different forms of 121, 165, 189 and 206 amino acids due to alternative splicing, which are designated as VEGF121, VEGF165, VEGF189, and VEGF206, respectively.

VEGF121 and VEGF165 are soluble that can be incorporated onto the vascular graft of the present invention. In one embodiment, VEGF121 and/or VEGF165 are mixed with a substrate, such as collagen, heparinized collagen, crosslinked collagen, crosslinked heparinized collagen, blood clot, drug, or the like, prior to be incorporated onto the vascular graft. In another embodiment, the method for incorporating the vascular endothelial growth factor comprises a step of impregnating the growth factor onto the vascular graft. In a further preferred embodiment, the step further comprises applying pressure to force impregnating the vascular endothelial growth factor into the vascular graft, preferably from the inner side or the blood-contacting side of the vascular graft.

VEGF189 and VEGF206 are bound to heparin containing proteoglycans in the cell surface. Therefore, a heparinized medical material, such as the one disclosed by Noishiki et al. (U.S. Pat. Nos. 4,806,595 and 5,387,236), has the capability of incorporating the desired vascular endothelial growth factor by binding VEGF189 and/or VEGF206 for site-specific angiogenesis. Both patents are included herein by reference. The vascular endothelial growth factor of the present invention may be selected from the group consisting of VEGF, VEGF 2, bFGF, VEGF121, VEGF165, VEGF189, and VEGF206.

The "platelet derived growth factor" in this invention may cover broadly PDAF (platelet derived angiogenesis factor), PDGF (platelet derived growth factor), TGF-B (transforming growth factor beta), PDEGF (platelet derived epidermal growth factor), PDWHF (platelet derived wound healing formula), and the like. The platelet derived growth factor of the present invention may also comprise any substrate that contains at least one of the above-referred PDAF, PDGF, TGF-B, PDEGF or PDWHF that possess angiogenesis activity, wherein said substrate may comprise blood clot or blood components. U.S. Pat. No. 5,599,558 to Gordinier et al. discloses general properties and constituents of platelet derived growth factor, and the patent is incorporated herein by reference.

The "tissue treatment factor" in this invention may refer to any chemical, substrate, material, and solution that may treat a tissue to render the tissue more angiogenic or have more angiogenesis propensity. A tissue treated by a polyepoxy compound or combinations of polyepoxy compounds, as disclosed in U.S. Pat. No. 4,806,595 has angiogenesibility. A vascular graft incorporating tissue treatment factor would render the medical device with enhanced angiogenesis. The entire content of the patent is incorporated herein by reference.

In accordance with the preferred embodiment of the present invention, the vascular graft may be selected from the group consisting of autologous graft, homograft, biological graft, synthetic graft, composite graft or the like. Furthermore, the biological graft or conduit is selected from the group consisting of internal mammary artery, umbilical vein, urethra, pericardium, jagular vein, genetically altered blood vessel, and combinations thereof. The vascular graft may be either heparinized or crosslinked, wherein an agent for crosslinking the vascular graft may be selected from the group consisting of glutaraldehyde, formalin, dialdehyde starch, polyepoxy compounds, and the like. The vascular graft of the present invention comprises site-specific angiogenesis factor adapted for enhancing angiogenesis.

In a still preferred embodiment, a method for treating diabetic foot of a patient comprising implanting a vascular graft for enhancing blood perfusion, wherein said vascular graft comprises site-specific angiogenesis factor. The angiogenesis factor may be selected from the group consisting of VEGF, VEGF 2, bFGF, VEGF121, VEGF165, VEGF189, VEGF206, PDGF, PDAF, TGF-B, PDEGF, PDWHF, polyepoxy compounds, and combination thereof Furthermore, a process for implanting a vascular graft having site-specific angiogenesis factor comprises (a) preparing an implantation site; (b) positioning the vascular graft at the implantation site; and (c) implanting the vascular graft. After the graft is in place, the endothelial cells and cells progenitors deposit site-specifically on the device for expedited angiogenesis and mitosis. The vascular graft for the implantation process may comprise at least one vascular endothelial growth factor or platelet derived growth factor, wherein the vascular graft may be selected from the group consisting of autologous graft, homograft, biological graft, synthetic graft, and composite graft.

DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 6, what is shown is an embodiment of a vascular graft having site-specific angiogenesis factor comprising at least one factor of the following: vascular endothelial growth factor, platelet derived growth factor, tissue treatment factor, or combination thereof.

Figure 1:
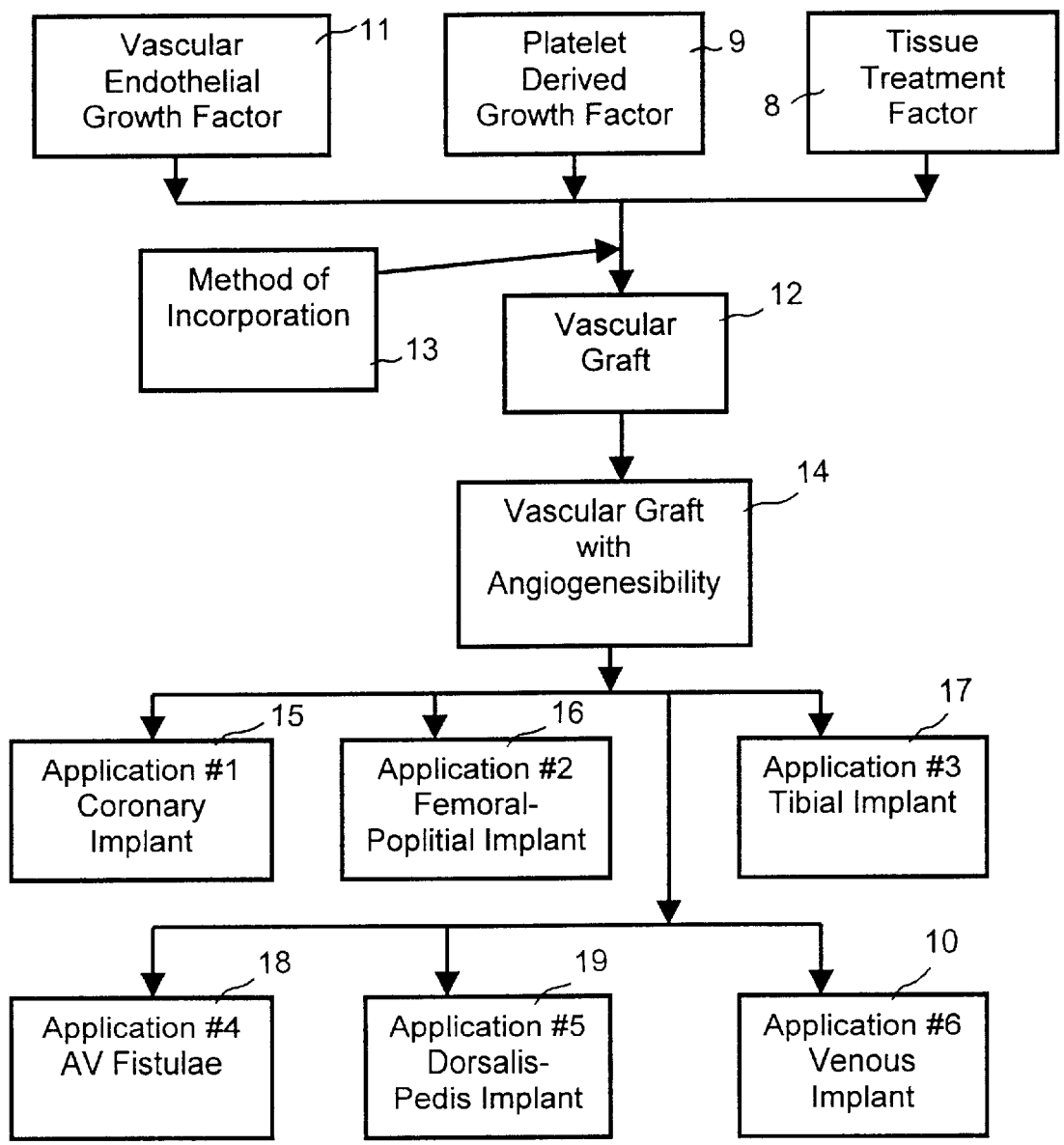
FIG. 1 is a schematic diagram illustrating the steps of preparing a vascular graft with angiogenesibility in accordance to the principles of the present invention.

FIG. 1 shows a schematic diagram illustrating the steps of preparing a vascular graft with angiogenesibility in accordance to the principles of the present invention. A vascular graft is a biocompatible material that may be used to fill, fix, replace, substitute, treat, or repair a part of the diseased/dysfunctional blood vessels. In one embodiment, the vascular graft comprises site-specific angiogenesis factor adapted for enhancing angiogenesis. In one preferred embodiment, the angiogenesis factor may be a polyepoxy compound or combination of polyepoxy compounds. In another embodiment, the angiogenesis factor may be selected from the group consisting of VEGF, VEGF 2, bFGF, VEGF121, VEGF165, VEGF189, VEGF206, PDGF, PDAF, TGF-B, PDEGF, PDWHF, and combination thereof. In a further embodiment, the vascular graft is selected from the group consisting of autologous graft, homograft, biological graft, synthetic graft, composite graft, and the like.

Vascular endothelial growth factor is obtained from a quality manufacturer or prepared according to the available techniques/protocols in the art. At least one vascular endothelial growth factor 11 is incorporated onto the vascular graft 12 by a method of incorporation 13. Other angiogenesis factor, such as platelet derived growth factor 9 or tissue treatment factor 10 may also be used in the present invention. In one embodiment, the method of incorporation may comprise mixing, suspending, or dispersing the angiogenesis factor with a substrate, such as collagen, heparinized collagen, crosslinked collagen, blood clot, blood, blood component, crosslinked heparinized collagen, drug, drug carrier, tubular conduit, their mixture, and the like. In another embodiment, the method of incorporation may comprise encapsulation of the angiogenesis factor as a drug or drug carrier. In still another embodiment, the method of incorporation may comprise impregnating, immersing, soaking, spraying, pressure impregnating, entrapping the angiogenesis factor into the vascular graft. The vascular graft with angiogenesibility 14 may be used as a vascular graft in various procedures such as coronary implant 15, femoral-poplitial implant 16, tibial implant 17, AV fistulae 18, dorsalis-pedis implant 19 or venous implant 10.

Collagen is a protein which is highly compatible with cells. Collagen used and defined in the present invention may comprise a soluble collagen, an insoluble collagen, a chemically modified collagen, a collagen derivative such as gelatin, a polypeptide chemically modified collagen, a collagen derivative such as gelatin, a polypeptide obtained by hydrolysis of collagen, and a natural collagen present in natural tissues.

Figure 2:
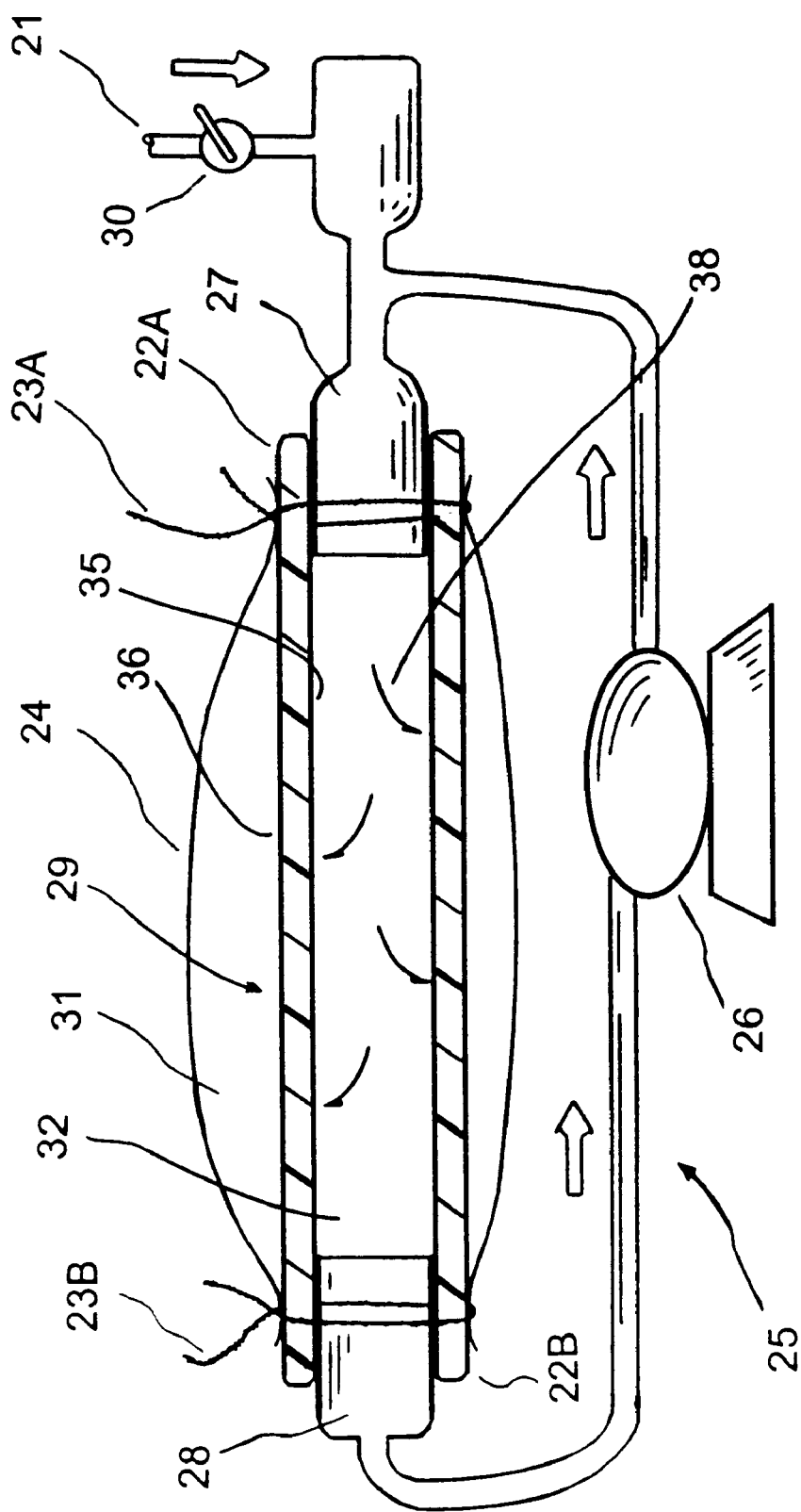
FIG. 2 is one embodiment of the process for preparing a vascular graft having angiogenesis factor at the inner wall of the vascular graft.

FIG. 2 shows one embodiment of the process for preparing a vascular graft having angiogenesis factor at the inner wall of the vascular graft. A vascular graft 29 comprises two end sections 22A, 22B, an inner wall 35, an outer surface 36 and a lumen 32. One end section 22A of the vascular graft 29 is wrapped around and over an inlet section 27 of a circulating impregnating system 25 tightly by a ligature 23A. Similarly, the other end section 22B of the vascular graft 29 is wrapped around and over an outlet section 28 of the circulating impregnating system 25 tightly by another ligature 23B. For a preferred impregnating method, a non-permeable radially expanded tubular arrangement 24 may optionally be used to facilitate a desired differential pressure across the wall of the vascular graft 29 between the lumen 32 and the outer space 31. The outer space 31 between the outer surface 36 of the vascular graft 29 and the tubular arrangement 24 can be vacuumed so as to generate the desired differential pressure for a forced impregnation method.

An impregnating medium containing at least one angiogenesis factor is introduced from the inlet port 21 into the circulating impregnating system 25. A pump 26 or the like may be used to circulate the impregnating medium through the lumen 32 of the vascular graft 29 so as to impregnate the angiogenesis factor onto or into the inner wall 35. In an alternate embodiment of forced impregnation method, the impregnating medium is introduced into the inlet port 21 at a pressure and maintained at an elevated pressure in the circulating impregnating system 25 by a control valve 30 next to the medium inlet port 21. The impregnating medium flows radially outwardly 38 from the lumen 32 towards the inner wall 35 of the vascular prosthesis. By doing forced impregnation or facilitated impregnation, the angiogenesis factor is firmly impregnated onto the vascular graft 29. The efficiency and completeness of impregnation may be affected by the flow rate of the circulating impregnating system, the concentration of angiogenesis factor in the impregnating medium, the differential pressure across the wall of the graft, and the characteristics of the angiogenesis factor employed.

Figure 3:
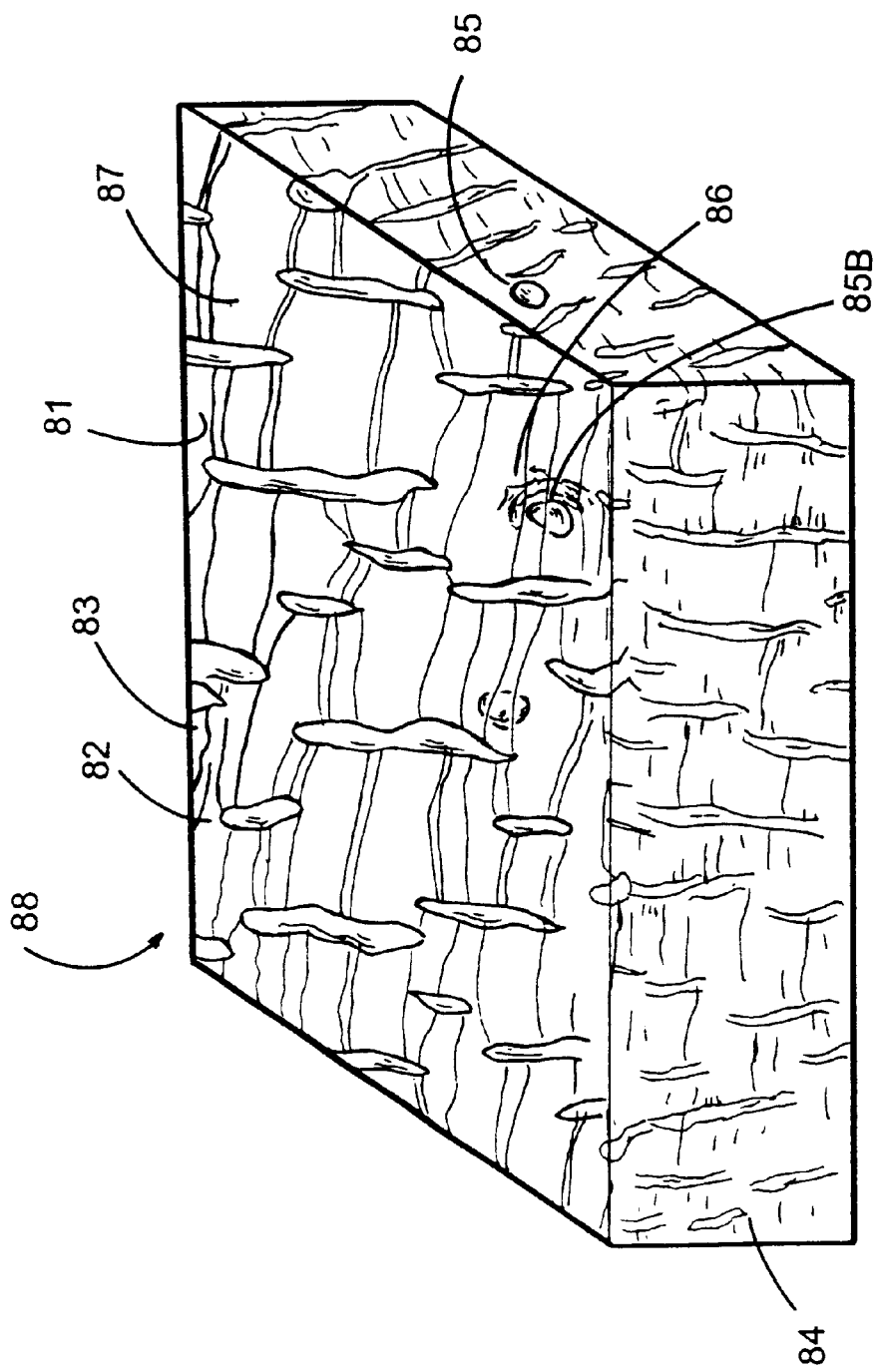
FIG. 3 is a preferred embodiment of the vascular graft incorporating site-specific angiogenesis factors at the inner side of the medical device.

FIG. 3 shows a preferred embodiment of the vascular graft having angiogenesis factors at the inner side and within the matrix of the vascular graft. The vascular graft of the present invention may comprise a synthetic graft made of synthetic material, such as expanded polytetrafluoroethylene (ePTFE) or polyester, a biological material or a blood vessel graft, such as autologous internal mammary artery, autologous saphenous vein or cryo-preserved allograft. A biological material of the present invention is usually crosslinked or tanned. A biological material or a biological graft may be crosslinked by glutaraldehyde, dialdehyde starch, formalin, other crosslinking agent, or the like. On the other hand, the biological material of the present invention is not crosslinked. The biological material or vascular graft of the present invention may be heparinized or rendered anti-thrombogenic.

As illustrated in FIG. 3, an ePTFE vascular graft comprises an interior surface or blood-contacting surface 81 and the interstices or matrix 84. The ePTFE vascular graft 88 comprises nodes 82, fibrils 83, and void 87 in-between the fibrils. The void volume or porosity of an ePTFE vascular graft may be as high as 85% air surrounded by 15% pure expanded PTFE material. Angiogenesis factor 85 is impregnated onto the vascular graft 88 at or close to the interior surface 81 by a method of incorporation discussed above. In accordance to an alternate embodiment, some of the angiogenesis factors 85B are impregnated onto the vascular graft along with a substrate 86, wherein the substrate may be selected from the group consisting of collagen, heparinized collagen crosslinked collagen, crosslinked heparinized collagen, blood clot, blood, tubular conduit, or the like. In one preferred embodiment, one method to incorporate the angiogenesis factor onto a vascular graft is to incorporate the angiogenesis factor on a tubular conduit, and wrap the tubular conduit onto the vascular graft thereafter to make a composite vascular graft of the present invention. The incorporated angiogenesis factor may also stay inside the interstices 84 not far away from the inner or interior surface 81. The angiogenesis factor thus has a site-specific therapeutical effect when the vascular graft is implanted.

Figure 4:
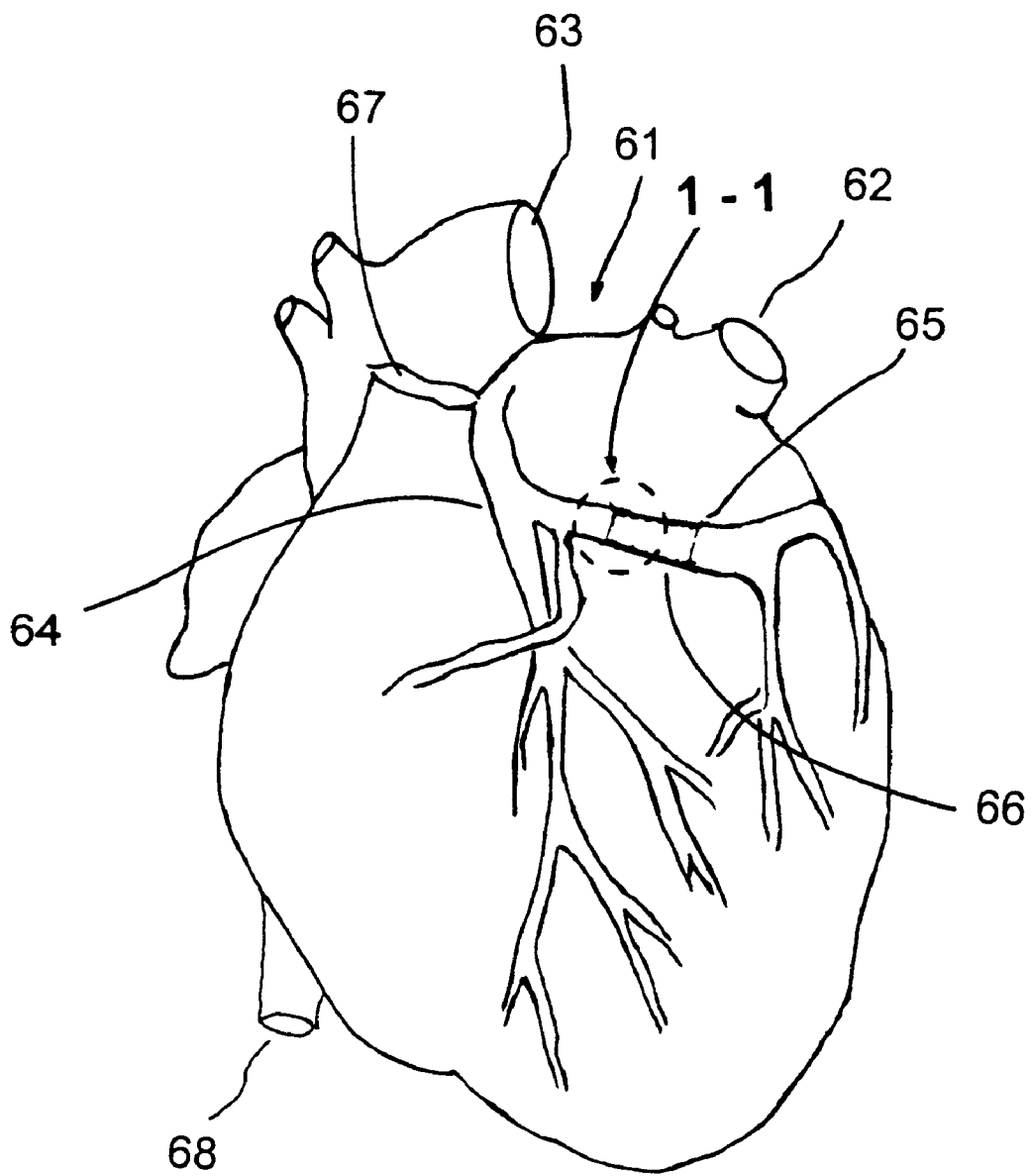
FIG. 4 is a perspective view of a coronary artery bypass grafting using a vascular graft of the present invention.

FIG. 4 shows a perspective view of a coronary artery bypass grafting using a vascular graft of the present invention. The heart 61 includes several vital blood vessels, such as coronary arteries, aorta 63, pulmonary artery 62, superior vena cava 67 and inferior vena cava 68. The coronary artery system includes left anterior descending coronary artery 64, left circumflex coronary artery 66 and coronary vasculature branches. A vascular graft 65 of the present invention is implanted to replace a portion of the diseased/dysfunctional coronary artery. Section 1—1 shows the junction region of the vascular graft 65 and its host coronary artery 66. The graft can also implanted as a bypass.

Figure 5:
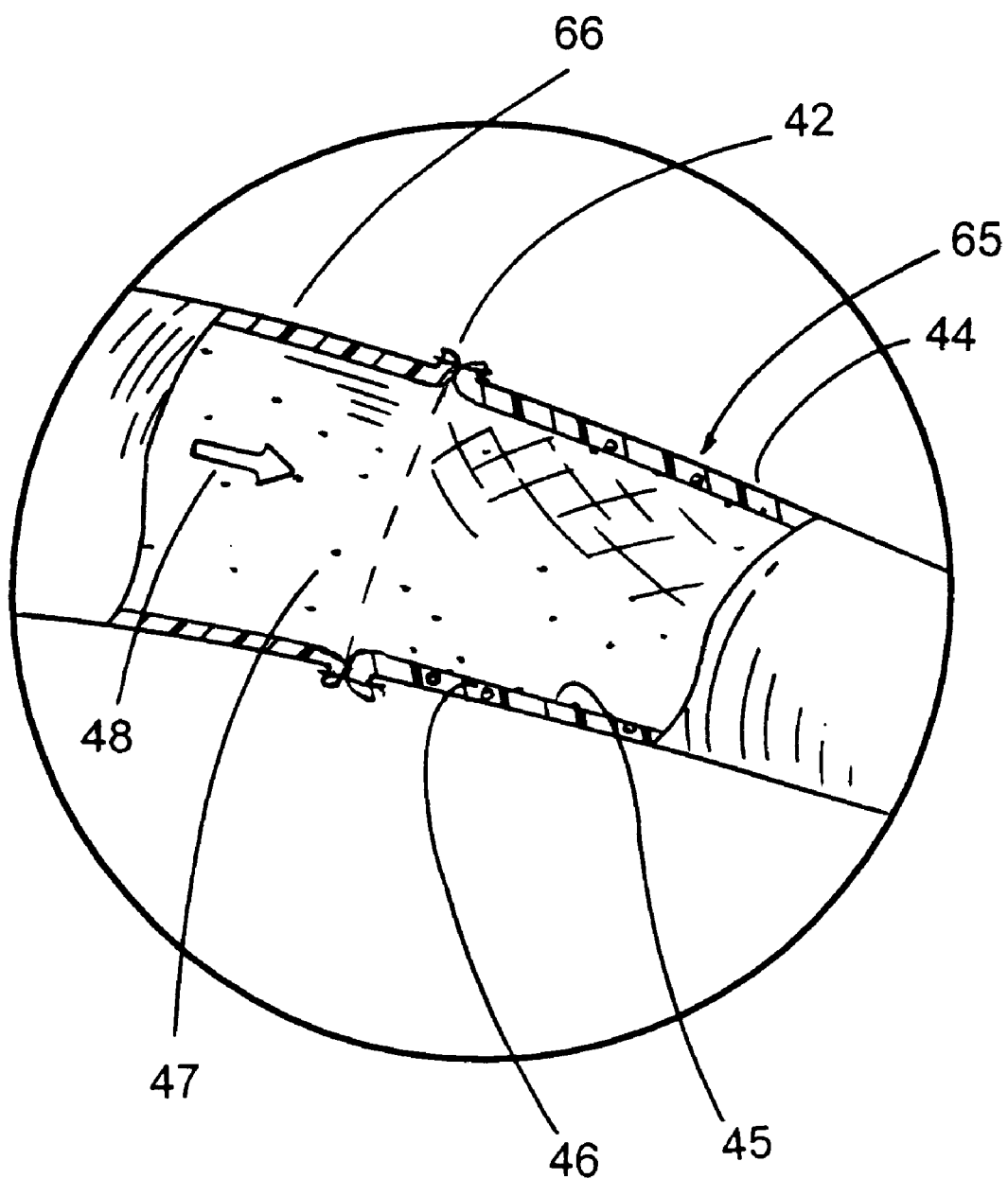
FIG. 5 is an enlarged view of the section 1—1 of FIG. 4, illustrating implantation of a coronary artery bypass graft according to the principles of the present invention.

FIG. 5 shows an enlarged cross-sectional view of the section 1—1 of FIG. 4, illustrating implantation of a coronary artery graft according to the principles of the present invention. The vascular graft 65 is sutured to its host artery 66 at an anastomosis 42. Different modes of suturing techniques may be employed, such as running suture, interrupted suture or the like. As shown in FIG. 5, blood flow 48 is in the direction from the host artery 66 toward the vascular graft 65. Blood usually contains red blood cells, white blood cells, platelet, proteins, plasma and small quantity of other cells and cells progenitor, such as free flowing endothelial cells 47, stem cells, $CD34^+$, and the like. The vascular graft 65 may comprise an inner wall 45 and an outer wall 44, wherein pre-incorporated angiogenesis factor 46 may stay or be entrapped at the inner wall 45 or within the wall. The incorporated angiogenesis factor 46 may promote the desired angiogenesis and/or neovascularization with any attracted endothelial cells inside the wall of the graft 65.

Figure 6:
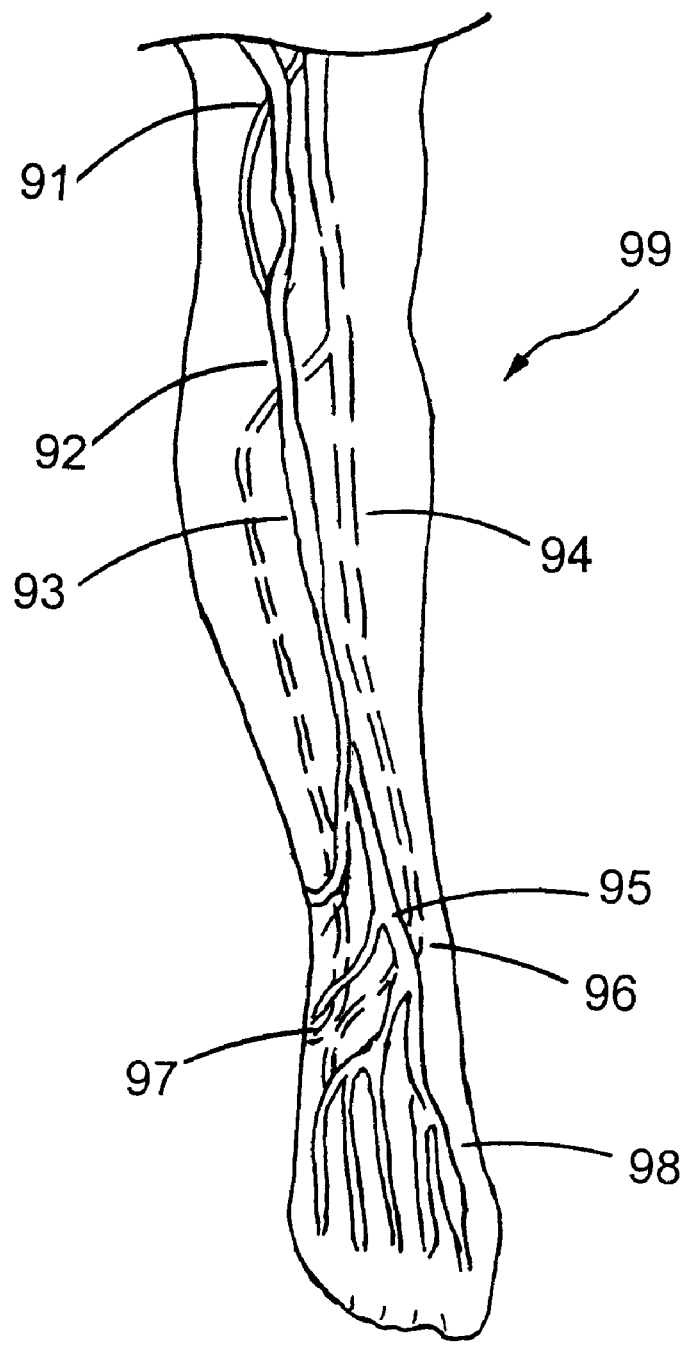
FIG. 6 is a perspective view of the lower extremity of a patient having diseased/dysfunctional arteries available for graft implantation leading to enhanced angiogenesis and diabetic foot treatment.

FIG. 6 shows a perspective view of the lower extremity 99 of a patient having diseased/dysfunctional arteries available for graft implantation leading to enhanced angiogenesis and diabetic foot treatment. The major arteries that may become dysfunctional for a diabetes patient include poplitial artery 91, fibular artery 92, anterior tibial artery 93, posterior tibial artery 94, dorsalis pedis artery 95, medial plantar artery 96, lateral plantar artery 97, digital artery 98, and the like. In one embodiment, a method for treating diabetic foot of a patient comprises implanting a vascular graft for enhanced blood perfusion, wherein the vascular graft comprises site-specific angiogenesis factor. The vascular graft may be implanted for enhanced blood perfusion and angiogenesis in a surgical procedure selected from the group consisting of coronary artery implant, femorofemoral artery implant, femoral-poplitial artery implant, femoro-tibial artery implant, fibular artery implant, tibial artery implant, plantar artery implant, dorsalis-pedis artery implant, AV fistulae, and venous implant.

A process for implanting a vascular graft having site-specific angiogenesis factor comprises the steps of preparing an implantation site; positioning said vascular graft at the implantation site; and implanting said vascular graft. The process may comprise a surgical procedure selected from the group consisting of coronary artery implant, femorofemoral artery implant, femoral-poplitial artery implant, femoro-tibial artery implant, fibular artery implant, tibial artery implant, plantar artery implant, dorsalis-pedis artery implant, AV fistulae, and venous implant.

From the foregoing description, it should now be appreciated that a vascular graft having site-specific angiogenesis factor and methods thereof has been disclosed. The vascular graft has site-specific angiogenesibility for enhancing peripheral revascularization or neovascularization for blood perfusion so as to save the diseased foot from amputation, in one example. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A composite vascular graft having a site-specific angiogenesis factor for enhanced angiogenesis comprising:
   a vascular graft; and
   a tubular conduit wrapped onto said vascular graft, wherein said tubular conduit is incorporated with an angiogenesis factor.

2. A composite vascular graft having a site-specific angiogenesis factor for enhanced angiogenesis comprising:
   a vascular graft; and
   a substrate coated onto the outside of said vascular graft, wherein said substrate is selected from the group consisting of collagen, heparinized collagen, crosslinked collagen and crosslinked heparinized collagen, and wherein said substrate is incorporated with said angiogenesis factor.

3. The composite vascular graft according to claim 1, wherein said angiogenesis factor is selected from the group consisting of VEGF, VEGF 2, bFGF, VEGF121, VEGF165, VEGF189, VEGF206, PDGF, PDAF, TGF-B, PDEGF, PDWHF, polyepoxy compounds, and combination thereof.

4. The composite vascular graft according to claim 1, wherein said vascular graft is implanted for enhanced blood perfusion and angiogenesis in a surgical procedure selected from the group consisting of coronary artery implant, femorofemoral artery implant, femoral-poplitial artery implant, femoro-tibial artery implant, fibular artery implant, tibial artery implant, plantar artery implant, dorsalis-pedis artery implant, arterial-venous fistulae, and venous implant.

5. The composite vascular graft according to claim 1, wherein a source of said biological graft is a biological tubular conduit.

6. The composite vascular graft according to claim 5, wherein said biological tubular conduit is selected from the group consisting of internal mammary artery, umbilical vein, urethra, pericardium, jugular vein, genetically altered blood vessel, and combinations thereof.

* * * * *